United States Patent [19]

Godfroid et al.

[11] 4,263,464

[45] Apr. 21, 1981

[54] STABILIZED COMPOSITIONS CONTAINING METHYLENE CHLORIDE

[75] Inventors: Marcel Godfroid, Wavre; Roger Gerkens, Braine-l'Alleud, both of Belgium

[73] Assignee: Solvay & Cie., Brussels, Belgium

[21] Appl. No.: 953,613

[22] Filed: Oct. 23, 1978

[30] Foreign Application Priority Data

Oct. 24, 1977 [FR] France .................................. 77 32188

[51] Int. Cl.$^3$ ............................................. C09D 9/00
[52] U.S. Cl. .................................... 570/109; 252/171; 252/405; 252/407
[58] Field of Search ................. 260/652.5 R; 252/171, 252/405, 407

[56] References Cited

U.S. PATENT DOCUMENTS

| | | | |
|---|---|---|---|
| 1,904,450 | 4/1933 | Harris ............................ | 260/652.5 R |
| 2,008,680 | 7/1935 | Carlisle et al. ................. | 260/652.5 R |
| 2,106,158 | 1/1938 | Povenz et al. ................... | 252/171 |
| 3,887,628 | 6/1975 | Beckers .......................... | 260/652.5 R |
| 3,923,912 | 12/1975 | Beckers ......................... | 260/652.5 R |
| 3,989,640 | 11/1976 | Culver ........................... | 252/171 |
| 4,062,901 | 12/1977 | Lolivier et al. ................ | 260/652.5 R |

FOREIGN PATENT DOCUMENTS

741556 11/1969 Belgium .
781796 4/1972 Belgium .
773187 4/1957 United Kingdom .

OTHER PUBLICATIONS

W. L. Archer, *Ind. Eng. Chem. Prod. Res. Dev.*, vol. 18, No. 2, (1979), pp. 131–135.
Chemical Abstracts, vol. 83, 58070c, 58071d, (1975).

*Primary Examiner*—Winston A. Douglas
*Assistant Examiner*—J. V. Howard
*Attorney, Agent, or Firm*—Spencer & Kaye

[57] ABSTRACT

A methylene chloride composition is stabilized by hexamethylenetetramine, optionally mixed with one or more epoxides. The methylene chloride thus stabilized is very suitable for aerosol compositions containing large amounts of water.

9 Claims, No Drawings

STABILIZED COMPOSITIONS CONTAINING METHYLENE CHLORIDE

BACKGROUND OF THE INVENTION

The present invention relates to compositions comprising methylene chloride, which are stabilized in order to avoid the decomposition of the methylene chloride during its storage or during its use, and which are particularly suitable for aerosols.

Methylene chloride is frequently used in aerosol compositions as a solvent for the active materials, and as a depressant for the propellant (dichlorodifluoromethane, butane, propane, carbon dioxide, nitrous oxide and the like). However, methylene chloride tends to decompose, especially in contact with metallic surfaces and under the action of heat. The resulting corrosion of the metallic surfaces becomes particularly great when the aerosol compositions contain water in addition to the methylene chloride. This corrosiveness of methylene chloride is in particular very marked towards metals frequently used in the manufacture of aerosol cans, such as aluminum or tinplate.

It has already been proposed to counteract the damage to metallic surfaces by the halogenomethanes by adding to the latter small amounts of a stabilizer of an organic nature. Among the stabilizers which have been proposed for stabilizing chloromethanes such as methylene chloride, there may be mentioned various substances such as amylene (U.S. Pat. No. 1,904,450 in the name of DU PONT DE NEMOURS, filed on Mar. 3rd, 1931), phenol (U.S. Pat. No. 2,008,680 in the name of DU PONT DE NEMOURS, filed on Mar. 3rd, 1931), nitrated compounds (British Pat. No. 773,187, filed on Dec. 8th, 1955 in the name of FARBWERKE HOECHST AG), dimethoxymethane (Belgian Pat. No. 741,556, filed on Nov. 12th, 1969 in the name of DOW CHEMICAL CO.) and epoxides (U.S. Pat. No. 2,106,158 in the name of I. G. FARBEN, filed on July 4th, 1935).

The addition of these products to methylene chloride, however, does not make it possible to avoid the corrosion of the metallic surfaces when the methylene chloride is used as a mixture with water.

To overcome this disadvantage, it has been proposed to use synergistic mixtures of stabilizers. Among the mixtures of stabilizers which have been proposed for stabilizing methylene chloride, there may be mentioned the mixtures of 2-methylfuran with epoxides (Belgian Pat. No. 781,796, filed on Apr. 7th, 1972 in the name of SOLVAY & Cie.). These mixtures have provided particularly efficient for stabilizing methylene chloride in the presence of small amounts of water, of approximately a few percent relative to the methylene chloride. However, they do not make it possible to stabilize the methylene chloride sufficiently if it is stored in the presence of larger amounts of water.

SUMMARY OF THE INVENTION

The present invention aims to solve the problem of stabilizing methylene chloride in the presence of large amounts of water.

To this end, the present invention provides a composition containing methylene chloride stabilized by means of hexamethylenetetramine.

Hexamethylenetetramine (urotropine) corresponds to the formula

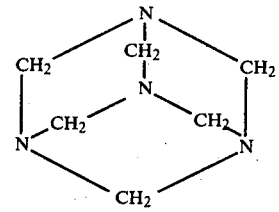

It is to be understood that both the foregoing general description and the following detailed description are exemplary, but are not restrictive of the invention.

DETAILED DESCRIPTION OF THE INVENTION

According to the present invention, the hexamethylenetetramine is in general employed at the rate of 0.0001 to 2%, and most frequently 0.001 to 1%, by weight of the methylene chloride present in the composition.

One or more epoxides can advantageously be added to the stabilizer used according to the present invention. The epoxides chosen are preferably those containing 2 to 8 carbon atoms. These epoxides can be substituted, for example by halogens, ether groups or hydroxyl groups. Most frequently, epoxides selected from among ethylene oxide, propylene oxide, epichlorohydrin, glycidol, butene oxides, pentene oxides, cyclohexene oxide, styrene oxide and methyl, ethyl, propyl, isopropyl and tert.-butyl glycidyl ether are used. The vicinal epoxides containing from 2 to 5 carbon atoms are particularly suitable. Among these, it is preferred to use propylene oxide, the butene oxides, glycidol, methyl glycidyl ether, ethyl glycidyl ether and epichlorohydrin. Propylene oxide, the butene oxides, glycidol and methyl glycidyl ether have proved particularly satisfactory.

According to the present invention, the epoxides are in general employed at the rate of 0.001 to 10%, and most frequently 0.01 to 5% by weight of the methylene chloride to be treated.

If hexamethylenetetramine and an epoxide are added simultaneously to the methylene chloride, these stabilizers are in general employed in a weight ratio of hexamethylenetetramine to epoxide of between 0.0001 and 1, and most frequently between 0.001 and 0.2. Different ratios can of course also be used.

It goes without saying that the use of hexamethylenetetramine, optionally mixed with one or more epoxides, which forms the subject of the present invention, can be combined with the use of one or more other known stabilizers.

Thus, one or more antioxidants such as alcohols and unsubstituted alkanes, cycloalkanes, alkenes and cycloalkenes can advantageously be added to the methylene chloride stabilized according to the invention. Advantageously, these antioxidants are added to methylene chloride stabilized by a mixture of hexamethylenetetramine with at least one epoxide.

The alcohols chosen are preferably those containing from 1 to 3 carbon atoms, such as methanol, ethanol, propanol and isopropanol. Ethanol has proved particularly satisfactory.

The alcohols are in general employed at the rate of 0.01 to 5%, and most frequently 0.05 to 3%, by weight of the methylene chloride to be treated.

The unsubstituted alkanes, cycloalkanes, alkenes and cycloalkenes which are chosen are preferably those which contain from 5 to 9 carbon atoms, such as n-pentane, isopentane, trimethylpropane, the dimethylbutanes, the dimethylpentanes, trimethylbutane, cyclohexane, cyclopentane, methylcyclopentane, ethylcyclopentane, methylcyclohexane, the pentenes, the dimethylbutenes, the methylbutenes, diisobutylene, the hexenes, the methylpentenes, tripropylene, cyclopentene, cyclohexene and methylcyclopentene. The alkanes, cycloalkanes, alkenes and cycloalkenes having a boiling point of between 0° C. and 120° C. are very suitable. Among these, it is preferred to use the pentenes, cyclohexane and n-pentane.

The alkanes, cycloalkanes, alkenes and cycloalkenes are in general employed at the rate of 0.0001 to 2% and most frequently 0.001 to 1% by weight of the methylene chloride to be treated.

The total amount of stabilizers and antioxidants employed is, in general, between 0.01 and 15% and most frequently between 0.05 and 10% by weight of the methylene chloride present in the composition.

The doses of the various stabilizers and antioxidants mentioned above are the most generally used doses. Lower doses can be used but are frequently less effective. Higher doses can also be used but are in general not justified and are of little interest from an economic point of view.

The present invention is also applicable to the stabilization of mixtures containing methylene chloride.

The methylene chloride stabilized according to the present invention has proved particularly stable and can advantageously be used in aerosol compositions having a high content of water which can, without disadvantage, be as much as five times the weight of methylene chloride. Most frequently, these compositions contain amounts of water which are between 5 and 200% by weight of the amount of methylene chloride employed.

The Example which follows and which does not imply any limitation shows the remarkable results obtained according to an embodiment of the invention.

EXAMPLE

In order to evaluate the effect of the stabilizer which forms the subject of the present invention on methylene chloride used as a depressant in aerosol cans containing large amounts of water, the corrosiveness of a homogeneous mixture containing a propellant (propane), a third solvent (ethanol), water and unstabilized methylene chloride (experiment 1R) or methylene chloride stabilized by means of an epoxide only (experiments 3R and 5R) was compared with that of the same mixture containing methylene chloride stabilized by means of hexamethylenetetramine alone or by means of a mixture of the latter with an epoxide (experiments 2, 4 and 6).

The experiment comprises introducing a composition containing 5% by weight of propane, 42% by weight of ethanol, 16% by weight of water and 37% by weight of stabilized or unstabilized methylene chloride into electrically-welded aerosol tinplate cans manufactured by SOBEMI and having a capacity of 280 cm³. The cans are filled to 75% of their capacity, are set up vertically and kept at 37° C. The general corrosion of the interior of the can is observed after two months.

Table I below shows the corrosion observed after two months when using the various stabilization formulations. The numeral 1 indicates that the appearance of the can is identical to that of the new can (no attack whatsoever); 2 indicates that there has been a slight generalized attack; 3 indicates that there has been a severe generalized attack; 4 indicates that there are a few pinholes and 5 that there are numerous pinholes (the letter r indicates the presence of patches of rust). The formulations carrying the letter R are given by way of comparison.

The amounts of stabilizers employed are expressed relative to the volume of methylene chloride.

TABLE I

| Experiment | Stabilizers | | | Extent of the corrosion |
|---|---|---|---|---|
| 1R | none | | | 2 + 5r |
| 2 | hexamethylenetetramine, | 0.1 | g/l | 4 to 5r |
| 3R | 1,2-epoxypropane, | 2 | g/l | 2 + 5r |
| 4 | { + hexamethylenetetramine, | 0.1 | g/l | 1 |
| | 1,2-epoxypropane, | 2 | g/l | |
| 5R | 1,2-epoxybutane, | 2 | g/l | 2 + 5r |
| 6 | { + hexamethylenetetramine, | 0.1 | g/l | 1 |
| | 1,2-epoxybutane | 2 | g/l | |

In all cases, the corrosion observed is present on the metal which is in contact with the liquid phase. In no case was any corrosion in the vapor phase observed.

Examination of Table 1 shows that, in the presence of large amounts of water, the unstabilized methylene chloride (experiment 1R) or the methylene chloride stabilized with epoxypropane (experiment 3R) or with epoxybutane (experiment 5R) causes considerable corrosion of the cans. In contrast, a noticeable reduction in corrosion is observed even if only very small amounts of hexamethylenetetramine are added (experiment 2). The simultaneous addition of an epoxide and of small amounts of hexamethylenetetramine makes it possible to suppress corrosion completely.

It will be understood that the above description of the present invention is susceptible to various modifications, changes and adaptations, and the same are intended to be comprehended within the meaning and range of equivalents of the appended claims.

We claim:

1. A methylene chloride composition containing hexamethylenetetramine and at least one epoxide as stabilizers for the methylene chloride.

2. A composition according to claim 1, wherein the amount of hexamethylenetetramine is between 0.0001 and 2% by weight of the methylene chloride.

3. A composition according to claim 1, wherein the epoxide is selected from epoxides containing from 2 to 8 carbon atoms.

4. A composition according to claim 3, wherein the epoxide is selected from propylene oxide, the butene oxides, glycidol and methyl glycidyl ether.

5. A composition according to claim 1, which further contains an antioxidant selected from the alcohols and the unsubstituted alkanes, cycloalkanes, alkenes and cycloalkenes.

6. A composition according to claim 5, wherein the alcohol is ethanol.

7. A composition according to claim 5, wherein the unsubstituted alkanes, cycloalkanes, alkenes and cycloalkenes are selected from n-pentane, cyclohexane and the pentenes.

8. A composition according to claim 1, which further contains water.

9. Compositions according to claim 8, wherein the water is present in an amount which can be as much as 5 times the weight of methylene chloride.

* * * * *